US00PP10873P

United States Patent [19]

Sherman

[11] Patent Number: Plant 10,873

[45] Date of Patent: May 4, 1999

[54] PLUM TREE NAMED 'GULFBLAZE'

[76] Inventor: Wayne B. Sherman, University of FL, P.O. Box 110690, Gainesville, Fla. 32611-0690

[21] Appl. No.: 08/958,255

[22] Filed: Aug. 5, 1997

[51] Int. Cl.[6] ..... A01H 5/00

[52] U.S. Cl. ..... Plt./184

[58] Field of Search ..... Plt./38.1, 184

[56] References Cited

U.S. PATENT DOCUMENTS

P.P. 10,116 11/1997 Gerawan ..... Plt./38.1

*Primary Examiner*—Howard J. Locker
*Assistant Examiner*—Kent L. Bell

[57] ABSTRACT

A Japanese type plum tree characterized by its low winter chilling adaptation to central and north Florida, and mid to late May ripening of dark red skin fruit with orange-yellow flesh and regular, high annual fruit production.

1 Drawing Sheet

BACKGROUND OF THE NEW VARIETY

The present invention relates to a new and distinct variety of plum tree, which will herein after be denominated varietally as 'Gulfblaze' plum tree which is adapted in flowering, foliation, and annual production to central and north Florida. Contrast is made to 'Gulfruby' plum for reliable description. This new variety is a promising candidate for commercial success in that it has disease resistance and adaptation for low to medium chill environments and produces red skin fruit ripening in mid to late May.

ORIGIN OF THE VARIETY

This invention relates to the discovery and asexual propagation of a new variety of Japanese-type plum tree, *Prunus salicina*, originating from the University of Florida stonefruit breeding program. 'Gulfblaze' originated from a 4$^{th}$ generation polycross of Florida selections. The original cross was made in 1967 by hybridizing 'Ozark Premier', 'Burbank', 'Beauty' and 'Bruce' with pollen from Taiwan, all un-patented. 'Taiwan' resulted from a seedling selection of a 1959 seed importation of 'Hung-ju' (unpatented) open pollinated. The present variety was selected as the 7$^{th}$ plum selection in 1987 and has been tested as Fla. 87-7.

Asexual Reproduction of the Variety

'Gulfblaze' has been asexually propagated by budding onto Flordaguard peach rootstock in our experimental orchard at Gainesville for three generations, which shows that characteristics are uniformly transmitted through succeeding generations.

SUMMARY OF THE VARIETY

This new and distinct variety of plum tree is large, vigorous, and semi-spreading in growth. It has an estimated winter chilling requirements of 250 chill units, but appears to have a high heat requirement for breaking dormancy. 'Gulfblaze' trees bloom before the earliest standard Japanese varieties at Gainesville, but with or after the earliest standard Japanese varieties in north Florida locations. Winter temperatures of 14F. in Florida have not damaged wood or flower and leaf buds. 'Golfblaze' is adapted to the mild winters of central and north Florida, flowering with 'Gulfruby' (unpatented) plum and is cross pollinated by 'Gulfruby'. 'Gulfblaze' is an efficient pollinizer for 'Gulfruby' as neither are self fruitful. 'Gulfblaze' is a regular and productive bearer of medium large, firm, semi-freestone fruit with good eating quality and a sour skin. The fruit is further characterized by having deep burgundy skin, firm, orangish flesh and hanging on the tree 10 days after maturity (shipping ripe) and ripening 7 to 10 days after 'Gulfruby'. Fruit set is very high and heavy fruit thinning may be required to prevent limb breakage and size fruit properly. This new variety is distinguished from 'Gulfruby' in a higher degree of resistance to bacterial leaf spot (*Xanthomonas campestris*) on leaves, twigs, and fruit, orange flesh, larger fruit, and later ripening. Fruit of 'Gulfblaze' are highly resistant to sunscald, concentric skin cracks, and split stones. Leaves have moderate resistance to leaf scald (*Xylella fastidiosa*).

BRIEF DESCRIPTION OF THE DRAWING

The accompanying drawing is a color photograph which illustrates a typical stem and leaves, and ripe fruit as viewed from the stem and distal ends, and side views perpendicular and parallel to the suture. The photograph was taken at the time the fruit was picked (shipping ripe) and the colors are as nearly true as is reasonably possible in a color representation of this type.

DETAILED BOTANICAL DESCRIPTION

The following is a detailed botanical description of 'Gulfblaze' plum tree, its foliage, flowers, and fruit, based on observations of specimens grown at Gainesville, Fla. on Flordaguard peach rootstock. Color names with capital letters designate values based upon the Pantone Book of Color published in 1990 by Harry N. Abrams, Inc. N.Y.

Tree:

*Size.*—Large and in the upper range for a Japanese plum.

*Vigor.*—Vigorous and in the upper range for a Japanese plum.

*Form.*—Semi-spreading.

*Density.*—Medium dense in branching habit and in the middle range for a Japanese plum.

*Shape.*—Rounded.

*Productivity.*—Productive and requires fruit thinning to prevent limb breakage and size fruit.

*Bearing.*—Regular and uniform on both spurs and whips.

*Cold hardiness.*—Hardy under Florida temperatures of 14F.

*Chilling requirement.*—Estimated 250 chill units based on bloom time and fruitfulness following annually diverse chilling in Florida. This is in the low range for Japanese plums.

Trunk:

*Size.*—Medium as trunk diameter is in the middle range for a Japanese plum.

*Texture.*—Medium shaggy, developing a moderate amount of peeling bark.

*Color.*—Lead Grey (Pantone 17-118).

Branch:

*Size.*—Medium diameters as scaffold branches are in the middle range for Japanese plum.

*Texture.*—Smooth.

*Lenticels.*—Medium number and in the middle range for a Japanese plum. 2 mm length and 0.5 to 1 mm width.

*Color.*—Pecan Brown (Pantone 17-1436) in 2 year wood and Green Oasis (Pantone 15-0538) in immature current seasons growth (whips).

*Fruiting.*—Fruits on spurs and branches (whips).

Leaves:

*Size.*—127 mm length (including petiole), 46 mm wide.

*Form.*—Wide elliptical with acuminate tip and acute base.

*Margin.*—Double serrate.

*Thickness.*—Medium and in the middle range for a Japanese plum.

*Surface.*—Upper, rugose; Lower, medium large veins.

*Texture.*—Glabrous.

*Petiole.*—14 mm length and Cedar (Pantone 16-0526), turning red in autumn.

*Glands.*—0 to 2 medium globose glands on upper portion of petiole or base of leaf blade.

*Color.*—Lower, Forest Green (Pantone 17-0230); Upper, Chive (Pantone 19-0323).

Flower buds:

*Size.*—Small and slightly shorter than leaf bud at the node.

*Length.*—Medium, 2 mm length.

*Form.*—Plump and free.

*Color.*—Dark Earth (Pantone 19-1020).

Flowers:

*Blossom period.*—About 10 days.

*Size.*—Small to medium for the range in Japanese plums.

*Pollen.*—Abundant and yellow.

*Color.*—White.

*Date.*—Bloom ranging February 5 to 15 at Gainesville.

*Aroma.*—Moderately scented and in the middle range for a Japanese plum.

Fruit:

*Maturity date.*—May 22–25 at Gainesville.

*Weight.*—75 to 80 grams.

*Size.*—Length 5.2 cm; Width 4.9 to 5.0 cm.

*Form.*—Round to slightly elliptic.

*Suture.*—Slightly furrowed at stem to the tip.

*Base.*—Nearly round, slightly flat.

*Apex.*—Round with furrow at suture.

*Cavity.*—Circular at top to bottom — 3 mm depth; 1 cm wide at top; 2 mm wide at bottom.

*Stem.*—Medium. 4 to 5 mm length.

Flesh:

*Texture.*—Firm and fine.

*Fibers.*—Texture.

*Flavor or eating quality.*—Sweet flesh with a tart skin.

*Juice.*—Juicy.

*Aroma.*—Lightly scented.

*Color.*—Apricot (Pantone 15-1153) to Marigold (Pantone 14-1450).

*Cavity.*—Small air pocket in flesh at stem end of the stone.

Skin:

*Thickness.*—Medium and in the middle range for a Japanese plum.

*Texture.*—Medium and in the middle range for a Japanese plum.

*Bloom (wax).*—Moderate and easily rubbed leaving shiny surface.

*Taste.*—Sour or tart.

*Color.*—Cardinal (Pantone 18-1643) at harvest.

Stone:

*Type.*—Semi freestone.

*Size.*—Length 2 cm. Width 1.6 cm.

*Form.*—Ovate.

*Base.*—Rounded.

*Apex.*—Acuminate.

*Sides.*—Equal.

*Ridges.*—1 to 2 mm ridges on dorsal and ventral sides.

*Color.*—Gold Earth (Pantone 15-1234).

Use. Local and long distance for fresh markets. The plum tree and its fruit herein described may vary slightly in detail due to climate, soil conditions, and cultural practices under which the variety may be grown.

We claim:

1. A new and distinct variety of plum tree, substantially as illustrated and described, which is vigorous, large, and semi-spreading in growth with a low winter chilling requirement for adaption to north central and north Florida producing an annual crop of medium large semi freestone fruit with full red skin and orange flesh, which ripens 7 to 10 days after 'Gulfruby' and having firm flesh with good fresh market shipping characteristics.

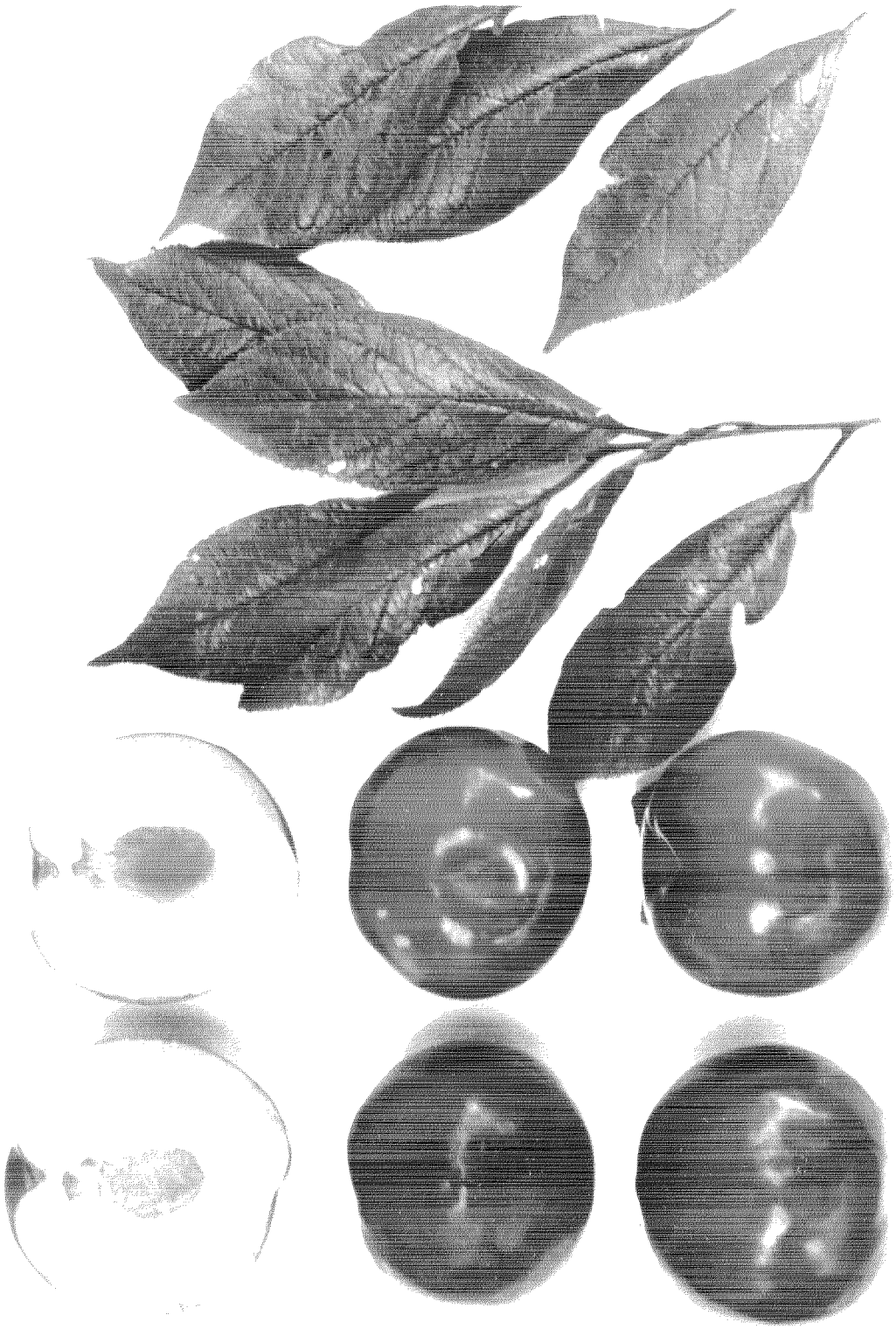

* * * * *